United States Patent [19]
Crystal et al.

[11] Patent Number: 6,159,950
[45] Date of Patent: Dec. 12, 2000

[54] METHOD OF MODULATING HAIR GROWTH

[75] Inventors: Ronald G. Crystal, Potomac, Md.; Noboru Sato, New York City, N.Y.; Philip L. Leopold, Basking Ridge, N.J.

[73] Assignee: Cornell Research Foundation, Inc., Ithaca, N.Y.

[21] Appl. No.: 09/174,506

[22] Filed: Oct. 16, 1998

[51] Int. Cl.[7] .................... A61K 48/00; C12N 15/85
[52] U.S. Cl. .................... 514/44; 514/880; 435/69.1; 435/320.1; 435/325; 435/375; 435/455
[58] Field of Search .................... 435/69.1, 320.1, 435/325, 375; 514/880, 44; 424/93.1; 536/23.1

[56] References Cited

U.S. PATENT DOCUMENTS

| | | | |
|---|---|---|---|
| 4,139,619 | 2/1979 | Chidsey, III | 424/45 |
| 4,596,812 | 6/1986 | Chidsey, III et al. | 514/256 |
| 5,424,398 | 6/1995 | Middeldorp et al. | 530/350 |
| 5,643,898 | 7/1997 | Grollier et al. | 514/169 |
| 5,656,300 | 8/1997 | Levin | 424/520 |
| 5,663,160 | 9/1997 | Meybeck et al. | 424/70.1 |
| 5,674,497 | 10/1997 | Kuwana et al. | 424/195.1 |
| 5,679,378 | 10/1997 | Fischer | 424/600 |
| 5,723,149 | 3/1998 | Bonte et al. | 424/450 |
| 5,739,111 | 4/1998 | Mahe | 514/18 |
| 5,741,816 | 4/1998 | Tsujihara | 514/547 |
| 5,750,107 | 5/1998 | Nomura | 424/195.1 |
| 5,753,713 | 5/1998 | Bass | 514/653 |
| 5,759,811 | 6/1998 | Epstein et al. | 435/69.1 |
| 5,767,152 | 6/1998 | Nielsen et al. | 514/26 |
| 5,789,543 | 8/1998 | Ingham et al. | 530/350 |
| 5,798,341 | 8/1998 | Klingelhöller | 514/52 |
| 5,800,477 | 9/1998 | Groux | 607/76 |
| 5,844,079 | 12/1998 | Ingham et al. | 530/350 |

FOREIGN PATENT DOCUMENTS

| | | |
|---|---|---|
| 0 335 554 | 10/1989 | European Pat. Off. |
| 353123 | 1/1990 | European Pat. Off. |
| 356271 | 2/1990 | European Pat. Off. |
| 408442 | 1/1991 | European Pat. Off. |
| 420707 | 4/1991 | European Pat. Off. |
| 0 455 422 | 11/1991 | European Pat. Off. |
| 459890 | 12/1991 | European Pat. Off. |
| 519819 | 12/1992 | European Pat. Off. |
| 522964 | 1/1993 | European Pat. Off. |
| WO 95/18856 | 7/1995 | WIPO. |
| WO 96/16668 | 6/1996 | WIPO. |
| WO 96/17924 | 6/1996 | WIPO. |
| WO 99/20298 | 4/1999 | WIPO. |
| WO 00/18428 | 4/2000 | WIPO. |

OTHER PUBLICATIONS

Dlugosz, JCI, 104:851–853, 1999.
Oro et al, Science, 276:817–821, 1997.
Fan et al, Nat. Med 7:788–92, 1997.
Sato et al, JCI 104:855–864, 1999.
Chin et al., *Developmental Biology*, 205 (1), 1–9 (1999).
Fan et al., *Nature Medicine*, 3(7), 788–792 (1997).
Morgan et al., *Developmental Biology*, 201, 1–12 (1998).
Alcedo et al., *Cell*, 86, 221–232 (Jul. 26, 1996).
Anderson et al., *Am. J. Human Genetics*, 19 (1), 12–22 (Jan. 1967).
Bain et al., *Gene Therapy*, 1, S68 (1994).
Barany et al., *Int. J. Peptide Protein Res.*, 30, 705–739 (1987).
Basler et al., *Nature*, 368, 208–214 (Mar. 17, 1994).
Belloni et al., *Nature Genetics*, 14, 350–356 (Nov. 14, 1996).
Berns et al., *Ann. N.Y. Acad. Sci.*, 772, 95–104 (1995).
Bertolino et al., "Biology of Hair Follicles" *in Dermatology in General Medicine*, pp. 289–293, Fitzpatrick et al., eds. (McGraw–Hill, 1993).
Bertolino et al., "Disorders of Epidermal Appendages and related disorders" *in Dermatology in General Medicine*, pp. 671–695, Fitzpatrick et al., eds. (McGraw–Hill, 1993).
Bitgood et al., *Developmental Biology*, 172, 126–138 (1995).
Blessing et al., *J. Cell. Biol.*, 135, 227–239 (1993).
Blessing et al., *Genes & Development*, 7, 204–215 (1993).
Bumcrot et al., *Mol. Cell. Biol.*, 15 (4), 2294–2303 (Apr. 1995).
Byrne et al., *Mol. Cell. Biol.*, 13, 3176–3190 (Jun. 1993).
Chang et al., *Development*, 120, 3339–3353 (1994).
Chiang et al., *Nature*, 383, 407–413 (Oct. 3, 1996).
Chuong et al., *J. Invest. Derm.*, 107, 639–45 (1996).
Cotsarelis, *Am. J. Pathol.*, 151, 1505–1509 (1997).
Dahmane et al., *Nature*, 389, 876–881 (1997).
Danilenko et al., *Mol. Med. Today*, 2, 460–467 (Nov. 1996).
Dean, *Nature Genetics*, 14, 245–247 (1996).
Domínguez et al., *Science*, 272, 1621–1625 (Jun. 14, 1996).
Echelard et al., *Cell*, 75, 1417–1430 (Dec. 31, 1993).
Ericson et al., *Cell*, 87, 661–673 (Nov. 15, 1996).
Fan et al., *Cell*, 81, 457–465 (May 5, 1995).
Federoff et al., *Proc. Natl. Acad. Sci. USA*, 89, 1636–1640 (1992).
Fietz et al., *Current Biol.*, 6, 643–650 (1995).
Fink et al., *Ann. Rev. Neurosci.*, 19, 265–287 (1996).
Gaillani et al., *Nature Genetics*, 14, 78–81 (Sep. 14, 1996).
Gat et al., *Cell*, 95, 605–614 (1998).
Guo et al., *EMBO J.*, 12, 973–986 (1993).
Guo et al., *Genes & Development*, 10, 165–175 (1996).
Hahn et al., *Cell*, 85, 841–851 (Jun. 14, 1996).
Hébert et al., *Cell*, 78, 1017–1025 (1994).
Holbrook et al., *J. Invest. Dermatol.*, 101 (1 Supp.), 39S–49S (Jul. 1993).

(List continued on next page.)

*Primary Examiner*—John L. LeGuyader
*Assistant Examiner*—Sumesh Kaushal
*Attorney, Agent, or Firm*—Leydig, Voit & Mayer, Ltd.

[57] ABSTRACT

The present invention concerns a method for modulating hair by affecting the hedgehog protein signal transduction pathway. In one aspect, the invention provides a method for promoting hair or attenuating hair loss by stimulating the hedgehog protein signal transduction pathway. In a second aspect, the invention provides a method of retarding hair growth or promoting hair loss by antagonizing the hedgehog protein signal transduction pathway. The method can also be used to control hair pigmentation.

8 Claims, No Drawings

U.S. PATENT DOCUMENTS

Honig, *Nature*, 291, 72–73 (May 7, 1981).
Hooper et al., *Cell*, 59, 751–765 (Nov. 17, 1989).
Hooper, *Nature*, 372, 461–464 (Dec. 1, 1994).
Hui et al., *Developmental Biology*, 162, 402–413 (1994).
Hynes et al., *Neuron*, 15, 35–44 (Jul. 1995).
Ingham, *Nature*, 366, 560–562 (Dec. 9, 1993).
Iseki et al., *Biochem. Biophys. Res. Commun.*, 218, 688–93 (1996).
Jiang et al., *J. Invest. Dermatol.*, 104, 523–525 (1995).
Jung et al., *Dev. Biol.*, 196 (1), 11–23 (1998).
Kallassy et al., *Cancer Res.*, 57, 4731–4735 (1997).
Kinto et al., *FEBS Lett.*, 404, 319–323 (1997).
Knudson, *Nature Genetics*, 5, 103–104 (Oct. 1993).
Korhonen et al., *Blood*, 86, 1828–1835 (1995).
Krauss et al., *Cell*, 75, 1431–1444 (1993).
Lee et al., *Cell*, 71, 33–50 (Oct. 2, 1992).
Lee et al., *Science*, 266, 1528–1537 (Dec. 2, 1994).
Lindner et al., *Am. J. Pathol.*, 151, 1601–1617 (1997).
Luckow et al., *Bio/Technology*, 6, 47 (1988).
Luetteke et al., *Cell*, 73, 263–278 (1993).
Maden, *Nature*, 371, 560–561 (Oct. 13, 1994).
Mann et al., *Cell*, 73, 249–261 (1993).
Marigo et al., *Genomics*, 28, 44–51 (1995).
Marti et al., *Nature*, 375, 322–325 (May 25, 1995).
McMahon et al., *Nature Medicine*, 2, 1308 (1996).
Merrifield, *J. Am. Chem. Soc.*, 85, 2149–2154 (1963).
Mohler et al., *Development*, 115, 957–971 (1992).
Nakano et al., *Nature*, 341, 508–513 (Oct. 12, 1989).
Niswander et al., *Nature*, 371, 609–612 (Oct. 13, 1994).
Nohno et al., *Biochem. Biophys. Res. Commun.*, 206 (1) 33–39 (1995).
Okada et al., *Am. J. Physiol.*, 275, F306–F314 (1998).
Oro et al., *Science*, 276, 817–821 (1997).
Oro et al., *Cell*, 95, 575–578 (1998).
Paus et al., *Lab. Invest.*, 60, 365–69 (1989)).
Paus et al., *Lab. Invest.*, 71, 134–140 (1994).
Peifer et al., *Cell*, 63, 1167–1178 (Dec. 21, 1990).
Peifer, *Science*, 272, 974–975 (May 17, 1996).
Perrimon, *Cell*, 86, 513–516 (Aug. 23, 1996).
Philpott et al., *J. Invest. Dermatol.*, 104 (5 Supp.), 44S–45S (May 1995).
Porter et al., *Nature*, 374, 363–366 (1995).
Riddle et al., *Cell*, 75, 1401–1416 (1993).
Roelink et al., *Cell*, 76, 761–775 (1994).
Roessler et al., *Nature Genetics*, 14, 357–360 (Nov. 1996).
St–Jaques et al., *Current Biology*, 8 (19), 1058–1068 (1998).
Schlaeger et al., *Proc. Nat. Acad. Sci. USA*, 94, 3058–3063 (1997).
Slominski et al., *J. Invest. Dermatol.*, 96, 172–179 (1991).
Slominski et al., *J. Invest. Dermatol.*, 101, 90S–97S (1993).
Slominski et al., *J. Invest. Dermatol.*, 102, 862–869 (1994).
Song et al., *Hum. Gene Ther.*, 8, 1207–1217 (1997).
Stenn et al., *Dermatol. Clin.*, 14, 167–196 (1996).
Sundberg et al., "The Waved–2 (wa2) Mutation, Chromosome 11," *JAX Notes*, 460, 2–5 (1995).
Tabata et al., *Cell*, 76, 89–102 (Jan. 14, 1994).
Tashiro et al., *Gene*, 183–189 (1993).
Ting–Berreth et al. *Developmental Dynamics*, 207, 157–70 (1996).
Ting–Berreth et al. *Developmental Biology*, 179, 347–59 (1996).
Tsukurov et al., *Nature Genetics*, 6, 282–286 (Mar. 1994).
Ungar, "Mouse sprouts extra hair follicles . . . ", *Biotechnology Newswatch*, p. 7 (Dec. 7, 1998).
Vassar et al., *Genes & Development*, 5, 714–727 (1991).
Vortkamp et al., *Science*, 273, 613–622 (Aug. 2, 1996).
Vu et al., *Cell*, 64, 1057–1068 (Mar. 22, 1991).
Wang et al., *Nature Medicine*, 1 (11), 1184–1188 (Nov. 1995).
Weninger et al., *Lab. Invest.*, 75, 647–657 (1996).
Williams et al., "Hairs" *in Gray's Anatomy*, pp. 90–94, P. L. Williams, et al., eds. (Churchill Livingston, 1989).
Williams et al., *Nature Genetics*, 7, 480–484 (1994).
Wolter et al., *Cancer Res.*, 57, 2581–2585 (1997).
Worgall et al., *Hum. Gene Ther.*, 8, 37–44 (1997).
Xie et al., *Nature*, 391, 90–92 (1998).

METHOD OF MODULATING HAIR GROWTH

TECHNICAL FIELD OF THE INVENTION

The present invention relates to a method for modulating hair growth.

BACKGROUND OF THE INVENTION

Hairs are filamentous, keratinized structures derived from the epidermis. Two broad categories of hairs are recognized: vellus hairs are short and narrow, and are present over most of the body surface; terminal hairs are longer, thicker, and often heavily pigmented. Terminal hairs include those of the scalp, eyebrows and eyelashes, post-pubertal hair of the axillae and pubis, and the facial and body hair of many men.

Each hair consists of a shaft and a root. The shaft is composed of specialized keratinocytes. The root lies within the hair follicle, which can extend deeply into the hypodermis or lie more superficially in the dermis. The proximal end of the root is expanded to form the hair bulb, which is indented on its deep surface by a conical vascular dermal papilla. The bulb comprises the germinative matrix and the keratogenous zone. The germinative matrix consists of a mass of pluripotent cells capping the dermal papilla; it is characterized by mitotic activity giving rise to the hair and its surrounding inner root sheath. Cells arising mitotically from this group move apically and differentiate along several different routes.

Follicular development relies on a series of messages between dermis and epidermis. During embryogenesis, the formation of hair follicles results from interactions between the epidermis and mesenchyme. The dermal components of the hair follicle (i.e., the dermal papilla and dermal sheath) are derived from an aggregate of mesenchymal cells. Follicle initiation and development begin with the aggregation of dermal fibroblasts and epidermal keratinocytes. The epidermal cells proliferate and penetrate the dermis as plugs. Subsequently, the epidermally derived cells encircle a dermal aggregation and incorporate it into a pocket of tissue, the dermal papilla. It is generally understood that the population of hair follicles and dermal papillae is established during embryogenesis with no significant postpartum development (P. L. Williams, et al., "Hairs" in *Gray's Anatomy*, pp. 90–94, P. L. Williams, et al., eds. (Churchill Livingston, 1989); D. H. Cormack, "Hairs" in *Ham's Histology*, 9 th Ed., D. H. Cormack, ed. (J. B. Lippincott Co., 1987)).

Hair growth is affected by proliferation of hair follicle matrix cells. Three distinct stages in the hair growth cycle are recognized: anagen, an active phase when hair growth occurs; catagen, the transition stage during which follicle activity declines; and telogen, the resting phase when no cell proliferation occurs. In the typical human scalp, anagen lasts several years, catagen lasts a few weeks, and the quiescent telogen phase lasts a few months (Bertolino et al., "Biology of Hair Follicles" in *Dermatology in General Medicine*, pp.289–93, Fitzpatrick et al., eds. (McGraw-Hill, 1993)). The timing of this renewal cycle differs between species and location within an animal. Following telogen, the hair falls out and another cycle begins. The various phases of the hair growth cycle are accompanied by characteristic changes in the thickness of the epidermis, dermis, and adipose layer. Additionally, in terminal hairs, anagen is accompanied by increasing melanogenesis as melanocytes in the hair follicle produce melanin that is incorporated into the hair shaft (Danilenko et al., Mol. Med. Today, 2, 460–67 (1996); Cotsarelis, *Am. J Pathol.*, 151, 1505–09 (1997) Slominski et al., *J. InvesL Dermatol.*, 101, 90 S–97 S (1993); Slominski et al., *J. Invest. Dermatiol.*, 96, 172–79 (1991)). Numerous factors affect this cycle. For example, various growth factors, steroid hormones, dermo-epithelial interaction, dermal vascularity, neuroectodermal factors, and the immune system have been implicated (see, e.g., Danilenko et al., supra; Cotsarelis, supra; Stenn et al., *Dermatol. Clin.*, 14, 167–96 (2996); Lindler et al., *Am. J Pathol.*, 151, 1601–17 (1997)).

Hair loss (alopecia) is a naturally occurring process in mammals; indeed, it is extremely common among healthy adult humans, especially men. Alopecia also can be induced by chemical agents or physical agents (e.g., during anti-cancer chemotherapy), and the condition also results from specific disease states and with increasing age. Alopecia typically is attributable to a disturbance in the hair renewal cycle, leading, at first, to acceleration of the frequency of the cycles, resulting in a shift in the population of follicles from the anagen phase to telogen. Normally, of the approximately 150,000 hairs on the typical human head, about 10% of them are in telogen at any given time; in skin undergoing alopecia, significantly more follicles are in telogen (Danilenko et al., supra). Ultimately, the hair follicles degenerate. This process manifests itself as a progressive thinning of the hair, first as a change of hair quality (i.e., more vellus and less terminal hair) and ultimately in a decrease in the number hairs in the affected area of skin.

In addition to hair loss, abnormally accentuated growth of hair can result from some rare conditions. For example, hirsutism is manifested as excessive androgen-dependent hair growth in women; hypertrichosis is an increase in androgen-independent hair growth (Bertolino et al., "Disorders of Epidermal 35 Appendages and related disorders" in *Dermatology in General Medicine*, pp. 671–95, Fitzpatrick et al., eds. (McGraw-Hill, 1993)). Such conditions can lead to profound social consequences for affected individuals.

As a result of the prevalence of alopecia, hirsutism, hypertrichosis, and other disorders, there is immense interest in the development of effective cosmetic and clinical treatments. However, despite such a need, effective prophylaxis and therapy remains elusive. For example, one method used to combat alopecia, hair transplant surgery, is not available to many people suffering from alopecia (e.g., patients having undergone chemotherapy, elderly individuals, etc.). Moreover, surgery offers, at best, only a partial remedy. Electrical stimulus has been suggested as an alternative way to promote hair growth (see, e.g., U.S. Pat. No. 5,800,477 and references cited therein); however, such methods are of questionable efficacy.

Other methods employ various chemical compounds, mud preparations, plant extracts, and the like in an effort to modulate the growth of hair (see, e.g., U.S. Pat. Nos. 5,798,341, 5,767,152, 5,753,713, 5,750,107, 5,741,816, 5,739,111, 5,723,149, 5,679,378, 5,674,497, 5,663,160, 5,656,300, 5,643,898, 4,139,619, and references cited therein). For example, one compound currently in clinical use for treating alopecia is 2,4-diamino-6-piperidinopyrimidine 3-oxide (i.e., minoxidil) or its derivatives (see, e.g., U.S. Pat. No. 4,596,812, European Patent Documents 353,123, 356,271, 408,442, 522,964, 420,707, 459,890 and 519,819). However, topical application of minoxidil and other agents is only partially effective and suffers from a number of disadvantages. For example, minoxidil is a vasodilatory drug which has serious side effects in many patients. Similarly, mud preparations and plant extracts can produce unwelcome side effects in various patients and are of questionable efficacy. Moreover such treatments require a normal scalp with no local abrasions, dermatitis, or sunburn, rendering such methods unavailable to many individuals. In view of the foregoing problems, there exists a need for a method for modulating hair growth

BRIEF SUMMARY OF THE INVENTION

The present invention concerns a method for modulating hair growth by affecting the hedgehog (HH) protein signal transduction pathway. In one aspect, the invention provides a method for promoting hair or attenuating hair loss by stimulating the HH pathway. In a second aspect, the invention provides a method of retarding hair growth or promoting hair loss by antagonizing the HH pathway. The method can also be used to control pigmentation within hair. These and other advantages of the present invention, as well as additional inventive features, will be apparent upon reading the following detailed description.

DETAILED DESCRIPTION OF THE INVENTION

The HH protein signal transduction pathway has been extensively researched in mammals (see, e.g., Dean, *Nature Genetics*, 14, 245–47 (1996); McMahon et al., *Nature Medicine*, 2, 1308 (1996)). Without being bound by any particular theory, the mammalian HH pathway within hair follicles appears to mirror the well-researched HH signaling pathway in Drosophila. In this pathway, a member of the HH family of proteins acts as an intercellular signaling molecule. At least three mammalian HH proteins have been identified - Sonic Hedgehog (SHH), Indian Hedgehog (1 HH), and Desert Hedgehog (DHH) (see, e.g., Echelard et al., *Cell*, 75, 1417–30 (1993); Krauss et al., *Cell*, 75, 1431–44 (1993); Riddle et al., *Cell*, 75, 1401–16 (1993); Chang et al., *Devel.*, 120, 3339–53 (1994); and Roelink et al., *Cell*, 76, 761–75 (1994)). The HH protein interacts with the target cell via a membrane-bound protein, Patched (Ptc). Ptc appears to function as an inhibitor of another membrane-bound protein, Smoothened (Smo), which is similar to many G-protein-coupled receptors. Binding of HH to Ptc, in turn, permits activation of Smo, thereby unleashing a cascade of downstream events. The HH signal transduction pathway converges ultimately on members of the Gli-family of zinc-finger transcription factors. Immediate regulation of the Gli proteins involves activation by Fused (Fu) and inhibition by Suppresser ofFused (SuFu) and Costal2 (Cos2). Once activated, the Gli proteins enter the nucleus and either activate (Gli1 or Gli2) or inactivate (Gli3) target genes. Genes likely activated by the HH pathway include Rtc, Wnt proteins (e.g., Wnt1 and Wnt10b), growth factors such as members of the TGF family (e.g., bone morphogenic proteins, TGFα, TGFβ), epidermal growth factors (e.g., EGF-R), fibroblast growth factors (e.g., FGF-5), kertinocyte growth factors (e.g., KGF), vascular endothelial growth factors (e.g., VEGF), hepatocytic nuclear factor 3β (HNF3β), and parathyroid hormone-related protein (PTHrP), many of which are implicated in the hair-growth cycle (see, e.g., Leukette et al., *Cell*, 73, 263–78 (1993); Vassar et al., *Genes. Devel.*, 5, 714–27 (1991); Mann et al., *Cell*, 73, 249–61 (1993); Sundberg et al., *Chromosome* 11 Jax Notes, 460, 2–5 (1995); Herbert et al., *Cell*, 78, 1017–25 (1994); Guo et al., *Genes Devel.*, 10, 165–75 (1996); Guo et al., *EMBO J.*, 12, 973–86 (1993); Lachgar et al., *Cell Biol. Toxicol.*, 12, 331 (1996); and Weninger et al., *Lab. Invest.*, 75, 647–57 (1996)).

The inventive method of modulating hair growth can be used in several contexts. For example, promoting hair growth or attenuating hair loss serves to combat the effects of alopecia in humans and other mammalian species. Conversely, retarding hair growth or promoting hair loss can combat the effects of hirsutism, hypertrichosis, and similar disorders within afflicted individuals. Additionally, the method can be employed to modulate hair growth and pigmentation in normal skin. Thus, for example, the method can be employed in wool or fur production (e.g., applied to alpaca, beaver, calf, chinchilla, coyote, ermine, fisher, fitch, fox, lamb, llama, lynx, marten, mink, muskrat, nutria, opossum, otter, raccoon, Russian squirrel, sable, sheep and other fur- or wool-bearing mammals), to accelerate hair growth thereby permitting greater net annual wool production or reducing the time needed to produce mature pelts. Alternatively, the method can be employed to produce custom designs of bare skin or thin, thick, or variegated hair within the pelts of treated animals.

In a first aspect, the invention provides a method of promoting hair growth or attenuating hair loss within mammalian skin by stimulating the HH signal transduction pathway. In accordance with the method, an agonist of the HH signal transduction pathway is supplied to the skin under conditions sufficient to stimulate the HH signal transduction pathway within hair follicles and thereby promote the growth of or attenuate the loss of hair within the skin. The agonist can be any factor acting positively on the HH signal transduction pathway within the hair follicle cells. Thus, for example, the agonist can be an HH protein as defined herein, Smo, Fu, etc., including derivatives thereof as described below. Moreover, the agonist could be a small molecule that binds Pct in a manner analogous to HH (thereby permitting activation of Smo) or a small molecule that binds Smo directly to activate it. Other small molecule agonists can pass through cell membranes and act within the cell. Alternatively, the agonist can be a factor which down-regulates the production or activity of antagonists of the HH pathway (e.g., an antisense RNA molecule attenuating translation of oneor more antagonist of the HH pathway). Preferably, the agonist is an HH protein or a small molecule, because-it can be supplied to the skin generally (i.e., externally to the target cell) to affect the cells in the hair follicles. Where the agonist acts within the target cell, it is supplied via gene transfer technology, as described herein, to deliver the gene encoding the agonist to cells within the follicle. To this end, the genes for several suitable downstream agonists are known (see, e.g., Xie et-al., *Nature*, 391, 90–92 (1998) (constitutively-active Smo). Where an HH protein or small molecule is employed as the agonist, it can be supplied as a protein preparation or via gene transfer technology, as described herein.

As mentioned, a preferred agonist is an HH protein. As defined herein, an HH protein is any intercellular signaling protein related to the HH family of proteins, although the HH protein most preferably is a mammalian HH protein (e.g., IHH, DHH, or SHH). Each HH isoform has been isolated from several species, including humans, and the genes for such isoforms are also known (see, e.g., Marigo et al., *Genomics*, 28, 44–51 (1995); Echelard et al., supra; Krauss et al., supra; Riddle et al., supra). Moreover, the HH protein can be an active fragment of a wild-type HH protein. It is within the skill of the art to create active derivatives of wild-type HH proteins (i.e., derivatives retaining the ability to transmit appropriate intercellular signals), and many suitable derivative HH proteins (e.g., secreted or soluble proteolytic cleavage products or recombinant HH protein derivatives) have been created (see, e.g., Porter et al., *Nature*, 374, 363–66 (1995); Feitz et al., *Current Biol.*, 6, 643–50 (1995); U.S. Pat. No. 5,579,811; and Published International Applications WO 96/16668, WO 96/17924, and WO 95/18856).

While any HH protein can be employed in the context of the present invention, preferably the HH proteip is an SHH protein or derivative thereof, as SHH is involved during embryogenesis with the development of many polarized structures. Regardless of the species of HH protein employed, preferably it is syngeneic to the species of the mammal to be treated, and most preferably it is derived from the same strain as the skin to be treated (where applicable).

Aside from activating the HH signals transduction pathway, the inventive method can promlote hair growth or attenuate hair loss by mimicking the effects of an activated HH pathway within the hair follicles. Thus, in accordance with the inventive method, one or more of the factors produced as a result of normal activation of the HH pathway can supplied to the skin under conditions sufficient promote the growth of or attenuate the loss of hair within the skin. For example, such a factor can be TGFα, TGFβ, EGF-R, FGF-5, KGF, VEGF, HNF3β, PTHrP, etc. As such factors normally act intercellularly as signaling molecules, they can be supplied to the skin as protein preparations or via gene transfer technoly, as described herein.

In another aspect, the invention provides a method of retarding hair growth or promoting hair loss within mammalian skin by antagonizing the HH signal transduction pathway within hair follicle cells. In accordance with the method, an antagonist of the HH signal transduction pathway is supplied to the skin sufficient to antagonize the HH signal transduction pathway within the hair follicles and thereby retard the growth of or promote the loss of hair within the skin. The antagonist can be any factor acting negatively on the HH signal transduction pathway within the, hair follicle cells. Thus, for example, the antagonist can be a protein such as Ptc, SuFu, Cos2, etc., or derivatives of such proteins as described herein. Moreover, the agonist could be a small molecule that prevents HH binding to Pct (thereby preventing activation of Smo) or a small molecule that binds Smo directly to inactivate it. Other small molecule antagonists can pass through cell membranes and act within the cell. Alternatively, the antagonist can be a factor which down-regulates the production or activity of agonists of the HH pathway (e.g., an antisense RNA molecule attenuating translation of one or more agonist of the HH pathway or of one of the target genes activated by the HH signals transduction pathway). Most of these, and other, antagonists act within the folcile cells. Thus, they are supplied via gene transfer technology, as described within, to deliver the gene encoding the agonist protein to cells within the follicle. To this end, the genes for several suitable antagonists are known, and others are readily apparent to those of skill in the art. However, some potential antagonists act extracellularly (e.g., a soluble form of the Ptc protein which can act extracellularly by binding free HH proteins, a scavenger of a growth factor produced upon activation of the HH pathway, etc.). Where the antagonist can act extracellularly, it can be supplied either by gene transfer technology or within a suitable protein preparation.

In addition to affecting the amount of hair growth, the inventive method of modulating hair growth also affects the quality of hair within the area of treated skin. Thus, the invention provides a method of controlling hair pigmentation within mammalian skin. The method involves providing to the skin an agonist or an antagonist of the HH signal transduction pathway, or a factor produced as a result of normal activation of the HH pathway, as described above. The factor is supplied under any suitable conditions sufficient to affect hair pigmentation. The effect will vary depending on the degree of pigmentation, and the type of cells present, within the area of skin. Thus, for example, in some skin an agonist of the HH signal transduction pathway is provided to accentuate pigmentation in the hair. In other skin, an antagonist of the HH signal transduction pathway is provided, to decrease pigmentation in the hair.

In accordance with the inventive method, factors (i.e., agonists or antagonists of the HH signal transduction pathway or products of normal activation of the HH pathway) are supplied to mammalian skin either as protein preparations or via gene transfer technology. The protein sequences of many such factors are known, and their genes have been cloned. While any such wild-type factor can be used in the context of the present invention, it can alternatively be or comprise a derivative of a wild-type protein (e.g., an insertion, deletion, or substitution mutant, an active proteolytic cleavage product, etc.). Preferably, any substitution mutation is conservative in that it minimally disrupts the biochemical properties of the agonist or antagonist. Thus, where mutations are introduced to substitute amino acid residues, positively-charged residues (H, K, and R) preferably are substituted with positively-charged residues; negatively-charged residues (D and E) preferably are substituted with negatively-charged residues; neutral polar residues (C, G, N, Q, S, T, and Y) preferably are substituted with neutral polar residues; and neutral non-polar residues (A, F, I, L, M, P, V, and W) preferably are substituted with neutral non-polar residues.

Some protocols of the inventive method call for a given factor (i.e., agonists or antagonists of the HH signal transduction pathway or products of normal activation of the HH pathway) to be provided directly to the skin as protein. The protein for use in such protocols can be produced by any suitable method. For example, the protein can be synthesized using standard direct peptide synthesizing techniques (Bodanszky, *Principles of Peptide Synthesis*(Springer-Verlag, Heidelberg: 1984)), such as via solid-phase synthesis (see, e.g., Merrifield, *J. Am. Chem. Soc.*, 85, 2149–54 (1963); Barany et al., *Int J. Peptide Protein Res.*, 30, 705–739 (1987); and U.S. Pat. No. 5,424,398). Alternatively, a gene encoding the desired protein can be subcloned into an appropriate expression vector using well known molecular genetic techniques. The protein can then be produced by a host cell and isolated therefrom. Any appropriate expression vector (see, e.g., Pouwels et al., *Cloning Vectors: A Laboratory Manual*(Elsevior, N.Y.: 1985)) and corresponding suitable host cells can be employed for production of agonist or antagonist protein. Expression hosts include, but are not limited to, bacterial species, mammalian or insect host cell systems including baculovirus systems (see, e.g., Luckow et al., *Bio/Technology*, 6, 47 (1988)), and established cell lines such 293, COS-7, C127, 3T3, CHO, HeLa, BHK, etc. Once isolated, the protein is substantially purified by standard methods and provided to the skin within a suitable composition, as herein described.

In other protocols, the factor is provided to the skin through gene transfer technology. Such protocols employ an expression cassette including the appropriate gene. In addition to the desired coding sequence, the expression cassette also includes a promoter able to drive the expression of the gene within cells associated with skin (e.g., hair follicles). Many viral promoters are appropriate for use in such an expression cassette (e.g., retroviral ITRs, LTRs, immediate early viral promoters (IEp) (such as herpesvirus IEp (e.g., ICP4-IEp and ICPO-IEp) and cytomegalovirus (CMV) IEp), and other viral promoters (e.g., late viral promoters, Rous Sarcoma Virus (RSV) promoters, and Murine Leukemia Virus (MLV) promoters)). Other suitable promoters are eukaryotic promoters, such as enhancers (e.g., the rabbit β-globin regulatory elements), constitutively active promoters (e.g., the β-actin promoter, etc.), signal specific promoters (e.g., inducible and/or repressible promoters, such as a promoter responsive to TNF or RU486, the metallothionine promoter, etc.), and skin-specific promoters, such as keratin promoters for epidermal expression (Blessing et al., *Genes. Devel.*, 7, 204–15 (1993); Blessing et al., *J. Cell. BioL.*, 135, 227–239 (1993); Byrne et al., *Mol., Cell. Biol.*, 13, 3176–90 (1993)) tie-2 or von Willabrand factor promoters for endothelial expression (Korhonen et al., *Blood*, 86, 1828–35 (1995); Schlaeger et al., *Proc. Nat. Acad. Sci. (USA)*, 94, 3058–63 (1997)), collagen α1(I) or FSP1 promoters for mesenchymal expression (Okada et al., *Am. J. Physiol.*, 275, F306–14 (1998)), etc.

Within the expression cassette, the desired gene and the promoter are operably linked such that the promoter is able to drive the expression of the gene. As long as this operable linkage is maintained, the expression cassette can include more than one gene (e.g., multiple agonists or antagonists for a potentially synergistic effect). Furthermore, the expression cassette can optionally include other elements, such as polyadenylation sequences, ribosome entry sites, transcriptional regulatory elements (e.g., enhancers, silencers, etc.), or other sequences for enhancing the stability of the vector or transcript, or the translation or processing of the desired transcript within the cells (e.g., secretion signals, leaders, etc.).

For use in the inventive method, the desired expression cassette must be introduced into the cells in a manner suitable for them to express the gene contained therein. Any suitable genetic vector can be employed to introduce the expression cassette into the cells, many of which are known in the art. Examples of such vectors include naked DNA vectors (such as oligonucleotides or plasmids), viral vectors such as adeno-associated viral vectors (Berns et al., *Ann. N. Y Acad. Sci.*, 772, 95–104 (1995)), adenoviral vectors (Bain et al., *Gene Therapy*, 1, S68 (1994)), herpesvirus vectors (Fink et al., *Ann. Rev. Neurosci.*, 19, 265–87 (1996)), packaged amplicons (Federoff et al., *Proc. Nat. Acad. Sci. (USA)*, 89, 163640 (1992)), pappiloma virus vectors, picornavirus vectors, polyoma virus vectors, retroviral vectors, SV40 viral vectors, vaccinia virus vectors, and other vectors. Of these vectors, adenoviral vectors are preferred to provide rapid, transient expression of the gene. Indeed, expression of transgenes from adenoviral vectors in vivo generally ceases after about 1–3 weeks (see, e.g., Song et al., *Hum. Gene Ther.*, 8, 1207–17 (1997); Worgall et al., *Hum. Gene Ther.*, 8, 37–44 (1997)). The use of such vectors in the context of the present invention, thus, guards against risks of constitutive expression of many known agonists and antagonists of the HH signal transduction pathway or of the various end products associated with activation of the HH signal transduction pathway.

In addition to the expression cassette of interest, the vector also can include other genetic elements, such as, for example, genes encoding a selectable marker (e.g., β-gal or a marker conferring resistance to a toxin), a pharmacologically active protein, a transcription factor, or other biologically active substance.

The vector harboring the expression cassette is introduced into the cells by any method appropriate for the vector employed. Many such methods are well-known in the art. Thus, plasmids or oligonucleotide vectors are transferred by methods such as calcium phosphate precipitation, electroporation, liposome-mediated transfection, gene gun, microinjection, viral capsid-mediated transfer, polybrene-mediated transfer, protoplast fusion, etc. Viral vectors are best transferred into the cells by infecting them; however, the mode of infection can vary depending on the virus.

Cells into which the desired gene or genes have been transferred can be used in the inventive method as transient transformants. Alternatively, where the cells are cells in vitro, they can be subjected to several rounds of clonal selection (if the vector also contains a gene encoding a selectable marker, such as a gene conferring resistance to a toxin) to select for stable transformants. Within the cells, the gene is expressed such that the cells produce the desired product (e.g., protein or, in some cases, non-translated RNA). Successful expression of the gene can be assessed via standard molecular biological techniques (e.g., Northern or Western blotting, immunoprecipitation, enzyme immunoassay, etc.). Thus, for example, successful expression of an HH gene within the cells, provides the HH protein to the skin, within which it can act on hair follicle cells as an agonist of the HH pathway. Similarly, successful expression of a gene encoding a soluble Ptc protein provides the soluble Ptc protein to the skin, within which it can act as an antagonist of the HH pathway, as herein described.

In accordance with the inventive method, the factor (i.e., an agonist or antagonist of the HH signal transduction pathway or a product of normal activation of the HH pathway) is provided to the skin under conditions sufficient to modulate hair growth, hair loss, or pigmentation. To this end, the factor is provided to that area of skin in which modulation is sought. While, in some cases, such area of skin can be the entire surface of a mammal, the effect of the invention is limited to any area of skin to which the factor is delivered. The amount of the factor provided and time course will vary depending on the physical characteristics of the skin, the species of mammal, the age of the mammal, and the factor employed. However, some of the preferred agonists or antagonists of the HH signal transduction pathway are associated with carcinogenesis if expressed perpetually (see, e.g., Oro et al., *Science*, 276, 817–21 (1997); Wolter et al., *Cancer Res.*, 57, 2581–85 (1997); Williams et al., *Nat. Genet.*, 7, 480–84 (1994); Kallassy et al., *Cancer Res.*, 57, 4731–35 (1997)). Thus, it is preferable to confine exposure of the skin to the factor for a period of about a month or less (e.g., about 2–3 weeks or less), such as through the use of adenoviral vectors as described above. Of course, tiie time course of the invention is not limited to these periods, and the method can be repeated many times, if desired.

In many instances, the inventive method is applied to modulate hair growth and pigmentation to skin in vivo (i.e., on the surface of a mammal). A source of the desired factor (i.e., either a protein preparation of the factor or a vector containing appropriate expression cassette encoding the factor) can be applied topically to the surface of such skin in vivo (e.g., within a suitable composition). Alternatively, the source of the factor can be supplied to ski in vivo subdermally or intradermally. Where the factor need not act within follicle cells (e.g., an HH protein or a soluble Ptc protein), it can be supplied to the skin by transferring a vector containing an appropriate expression cassette to cells in vitro and subsequently introducing the cells into the skin. Other skin can be ex vivo ( .g., cultured artificial skin, a skin graft prior to engrafting, etc.). Many methods :f transferring the source of the desired factor to skin in vivo also apply to skin ex vivo. Additionally, the source of the factor can be supplied to skin ex vivo by bathing the skin in a composition comprising the source of the factor.

To facilitate the use of a source of the desired factor to modulate hair growth and pigmentation, it can be used in a pharmaceutical composition. Therefore, another aspect of the present invention is a pharmaceutical composition including such a source of the desired factor and a S itable carrier. The carrier includes one or more pharmaceutically (e.g., pharmacologically or physiologically) acceptable diluents, excipients, as well as optional au iliaries which facilitate processing of the active compounds into preparations whicli can be used pharmaceutically. Pharmaceutical compositions for use in th e present invention can be formulated in a conventional manner in accordance with i he route of administration chosen. Thus, for injection, the source of the desired fact or can be formulated in aqueous solutions, preferably in physiologically compatible buffers. For transmucosal administration, penetrants appropriate to the barrier to be permeated are used in the formulation. Other compositions can take such forms as suspensions, solutions or emulsions in oily or aqueous vehicles, and can contain f ormulatory agents such as suspending, stabilizing and/or dispersing agents. For application to the skin, the source of the desired factor can be formulated into a sui able gel, magma, creme, ointment, or other carrier. The source of the desired factor c n also be formulated into other pharmaceutical compositions such as those known in the art.

While one of skill in the art is fully able to practice the invention upon reading the foregoing detailed description , the following examples demonstrate its successful operation. In particular, the enamples demonstrate that providing an agonist of the HH signal transduction pa thway to mammalian skin promotes hair growth and modulates hair pigmentation. As these examples are included for purely illustrative purposes, they should not be construed to limit the scope of the invention in any respect.

The procedures employed in conducting the experiments referred to in the examples (e.g., animal handling techniques, Northern blotting techniques, manipulation and sequencing of DNA, virological methods) etc. are well-known in the art (see generally Sambrook et al., *Molecular Cloning, A Laboratory Manual*, Cold Spring Harbor Laboratory, Cold Spring Harbor, N.Y. (1989)). Accordingly, in the interest of brevity, elementary exerimental protocols are not discussed in detail.

EXAMPLE 1

This example demonstrates that transferring an expression cassette encoding an HH protein to mammalian skin result; in the accentuation of hair-specific gene expression within the skin.

An expression cassette was created, placing the entire cDNA for the murine SHH gene (Echelard et al., supra) under the control the HCMV immediate early promoter/enhancer and linked to the poladenylation sequence from SV40. By standard methods, this cassette was subcloned into the deleted E1 region of an E1$^-$/E3$^-$ adenovirus vector. Recombinant viruses avere isolated, and correct insertion of the expression cassette was verified by Southern hybridization and DNA sequence analysis. The recombinant vector (termed AdSHH) was thereafter purified and grown to high titer.

Groups of 2–4, 7 g, 3-week-old C57 Bl/6 mice were injected intradermally with $1\times10^8$ pfu of either AdSHH, a control E1$^-$/E3$^-$ vector lacking the SHH gene, or a sham injection of saline. After seven days skin in the area of injection was removed from the injected animals, as well as naive animals, and analyzed.

Northern hybridization of the excised skin patches revealed the presence of detectable levels of SHH mRNA in skin patches injected with AdSHH but not in sham-injected patches, naive patches, or patches injected with the E1$^-$/E3$^-$ control adenoviral vector.

Blots of mRNA from the various skin patches were also probed for the expression of genes known to be induced by the intercellular SHH signal (i.e., the Pct and Gli1 genes). Consistent with the pattern of SHH gene expression observed in the excised skin patches, Northern hybridizati on revealed the presence of detectable levels of Pct mRNA in skin injected with ikdSHH but not in sham-injected patches, naive patches, and patches injected with the E1$^-$/E3$^-$ control adenoviral vector. Some Gli1 mRNA was detectable in all skin patches; however, the amount of Gli1 signals was far more pronounced in the excised skin patches injected with AdSHH than in sham-injected patchys, naive patches, and patches injected with the E1$^-$/E1$^-$ control adenoviral vector.

Blots of mRNA from the various skin patches were also probed for the expression of hair-specific gene expression, specifically the hair-specific keratin gene (ghHb-1). Northern blots revealed the presence of some ghHb-1 mRNA in all excised skin patches; however, the level of ghHb-1 signal was far more pronounced in the skin injected with AdSHH than in sham-injected patches, naive patches, and patches injected with the E1$^-$/E3$^-$ control adenoviral vector.

These data indicate that the transfer of a gene encoding a HH protein can lead to expression of the HH gene within mammalian skin. That the expression of known response genes (e.g., Pct and Gli1) was accentuated reveals that transfer of the HH gene also transferred functional HH protein to the skin and stimulated the HH signal transduction pathway. Lastly, the results reveal that the transfer of a gene encoding a HH protein can leads to a dramatic accentuation of hair-specific genes within the skin.

EXAMPLE 2

This example demonstrates that transferring an expression cassette encoding an HH protein to mammalian skin promotes hair growth within the skin.

The excised skin patches described in Example 1 were visually examined to assess the effect of each treatment on hair growth in the area. To permit such evaluation, the mice were treated carefully during the protocol so as not to induce hair growth by the manner in which they were handled generally.

Melanogenesis, a pigment synthesis process that occurs in association with hair growth, was evaluated using digital image analysis. Specifically, light was passed through the excised patches and the intensity of transmitted light was measured by determining the average gray scale of a digitally collected image of the transmitted light. The optical density (relative light adsorbance) at the injection site was compared with the optical density of the same skin patch at a site distant from the injection site. This analysis revealed that the optical density of the excised skin patches that had been injected with AdSHH was consistently greater at the site of injection than distal from the injection or observed anywhere in sham-injected patches, naive patches, and patches injected with the E1$^-$/E1$^-$ control adenoviral vector.

The growth phase of the hair follicle cycle is associated with morphologic changes in follicles including an increase in size of the follicle, which can be recognized as an increase in the area of the follicle relative to total dermal/epidermal area. To evaluate hair follicle size, digital images of cross sections of skin patches were collected and analyzed by integrating the number of pixels occupied by either hair follicles or by total dermis/epidermis. The quotient of the two measurements gave the percentage of area occupied by hair follicles. This analysis revealed that the percentage of skin represented by mature hair follicles was consistently greater (between about 2 and about 4 fold) in the excised skin patches that had been injected with AdSHH than that observed in sham-injected patches,; naive patches, and patches injected with the E1$^-$/E3$^-$ control adenoviral vector.

These results indicate that transfer of a gene encoding an HH protein promotes hair growth in the skin. That follicular area increased suggests the presence of larger hair follicles in anagen phase that were actively producing hair shafts. This result is important given the fact that alopecia is often correlated with increased likelihood of finding hair follicles in telogen phase, and that AdSHH apparently induced anagen within a population of hair follicles initially in telogen. Another significant observation is that SHH gene expression did not induce the formation of any observed basal cell carcinoma in the test animals. Because the SHH gene has been implicated in such carcinogenesis (see, e.g., Dahmane et al., Nature, 389, 876–81 (1997)), the results observed in this study suggest that HH proteins and gene transfer protocols can be used to promote hair growth-or attenuate hair loss not only effectively, but safely as well.

EXAMPLE 3

This example demonstrates that transferring an expression cassette encoding an HH protein to mammalian skin affects melanogenesis within the skin and controls hair pigmentation.

In C57/Bl6 mice, anagen is marked by increased melanogenesis as melanocytes in the hair follicle produce melanin that is incorporated into the black hair shafts. Until the animals experience the first wave of anagen, they are light in color, after which they are black (Giang et al., *J. Invest. Dermatol*, 104, 523–25 (1995); Slominski et al., *J. Invest. Dermatol.*, 102, 862–69 (1994); Paus et al., *Lab. Invest.*, 71, 134–40 (1994); Paus et al., *Lab. Invest.*, 60, 365–69 (1989)). Melanin production requires the production of tyrosinase (Slominski et al., *J. Invest. Dermatol.*, 96, 172–79 (1991)).

RNA collected from the excised skin patches described above was assayed by Northern blot analysis for the presence of tyrosinase transcripts. Some tyrosinase mRNA was detectable in all skin patches; however, the amount of tyrosinase signals was far more pronounced in the excised skin patches injected with AdSHH than in sham-injected patches, naive patches, and patches injected with the E1$^-$/E3$^-$ control adenoviral vector. These results indicate that introducing an agonist of the HH signal transduction pathway modulates melanogenesis associated with hair follicle development

EXAMPLE 4

This example demonstrates that transferring an expression cassette encoding an HH protein to mammalian skin promotes hair growth within the skin.

The skin of mice treated as in Example 1 was examined after 5 days post injection. At such time, the hair of each mouse was died blonde to mark then-existing hair. Two days later, the mice were shaved and examined for the induction of melanogenesis associated with anagen skin. The dorsal skin of sham-injected mice, mice injected with the E1$^-$/E3$^-$ control adenoviral vector, and of untreated mice displayed no pigmentation. In contrast, mice injected with AdSHH all displayed profound melanogenesis in the area of the injection.

The animals were again examined at 14 days post-injection. At this time, the area of skin on the AdSHH had produced new (dark) hair shafts. In contrast, the surrounding area as well as all skin of the other mice, had only begun to enter anagen. These data demonstrate that introducing an agonist of the HH signal transduction pathway accelerates the rate of hair growth.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of promoting hair growth within mammalian skin, said method comprising providing to said skin a vector comprising a DNA sequence encoding an agonist of the hedgehog signal transduction pathway under conditions sufficient for said cells produce said agonist so as to stimulate said hedgehog signal transduction pathway and thereby promote the growth of said hair, wherein said agonist is a hedgehog protein.

2. The method of claim 1, wherein said hedgehog protein is a sonic hedgehog protein.

3. The method of claim 1, wherein said vector is an adenoviral vector.

4. The method of claim 1, wherein said cells are within a hair follicle.

5. The method of claim 1, wherein said skin is cultured in vitro.

6. The method of claim 1, wherein said skin is the skin of a fur- or wool-bearing mammal.

7. The method of claim 1, wherein said skin is the skin of a post natal mammal selected from the group of mammals consisting of alpaca, beaver, calf, chinchilla, coyote, ermine, fisher, fitch, fox, lamb, llama, lynx, marten, mink, muskrat, nutria, opossum, otter, raccoon, Russian squirrel, sable, and sheep.

8. The method of claim 1, wherein said skin is human skin.

* * * * *